Figure 1:
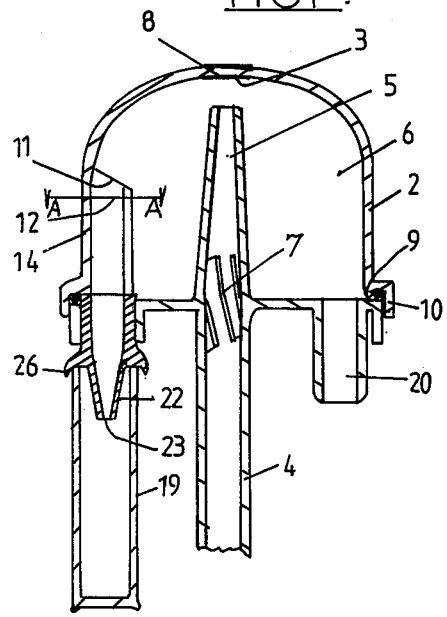

United States Patent [19]

Wenham

[11] 4,213,341
[45] Jul. 22, 1980

[54] APPARATUS FOR SAMPLING A FLOW OF LIQUID FROM A FLUID AT LEAST SOME OF WHICH IS A LIQUID

[75] Inventor: Douglas L. Wenham, Hamilton, New Zealand

[73] Assignee: AHI Operations Limited, Auckland, New Zealand

[21] Appl. No.: 966,731

[22] Filed: Dec. 5, 1978

[30] Foreign Application Priority Data

Dec. 9, 1977 [NZ] New Zealand ............... 185923
Dec. 9, 1977 [NZ] New Zealand ............... 185924
Dec. 9, 1977 [NZ] New Zealand ............... 185925

[51] Int. Cl.² ............................................. G01N 1/14
[52] U.S. Cl. ................................... 73/421 A; 173/202
[58] Field of Search ............... 73/421 R, 421 A, 202; 141/130

[56] References Cited

U.S. PATENT DOCUMENTS

| 2,355,620 | 8/1944 | Bower ........................... 141/130 |
| 3,349,617 | 10/1967 | Hartstone ..................... 73/202 |
| 3,481,197 | 12/1969 | Wenham ........................ 73/202 |
| 3,942,388 | 3/1976 | Ratnou ......................... 73/421 A |

FOREIGN PATENT DOCUMENTS 879026 6/1953 Fed. Rep. of Germany ........ 73/421 A

*Primary Examiner*—S. Clement Swisher
*Attorney, Agent, or Firm*—Holman & Stern

[57] ABSTRACT

A flow sampling apparatus has a body through which a central inlet conduit runs and a dome on the body. An inlet orifice on the inlet conduit discharges a fluid containing some liquid (milk) and the liquid flows evenly over the inner surface of the dome. One or more outlet ports are connected to a pair of intermediate vanes of a flow divider having at least four vanes and the liquid passing between the intermediate vanes is a representative sample of the whole flow over the inner surface of the dome. The sample is delivered to a sampling flask wither to the bottom of a flask which may be emptied by pressurizing the liquid in the flask or delivery may be by a flexible tube to a selected one of a series of flasks held in a removable magazine.

7 Claims, 16 Drawing Figures

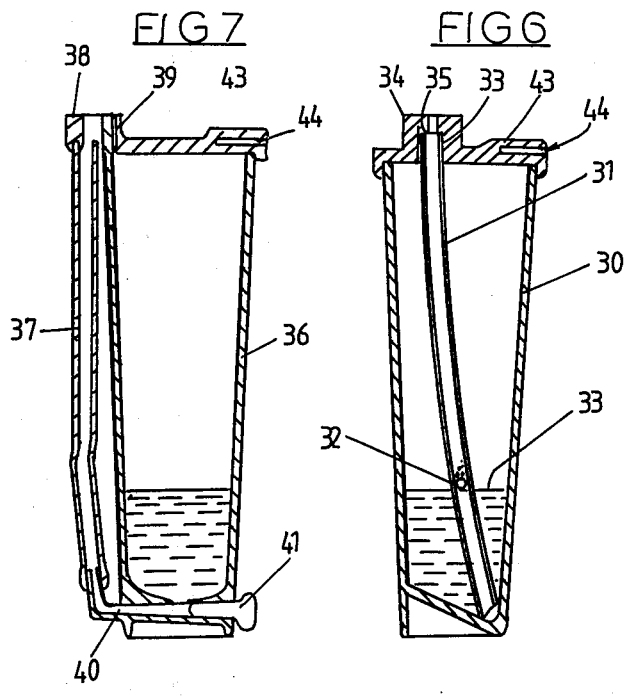
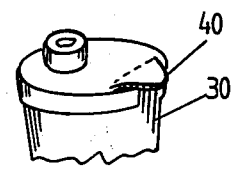
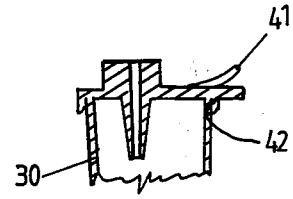
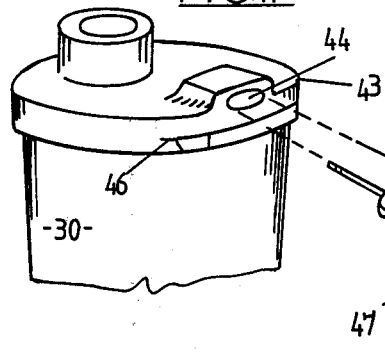
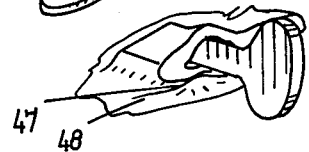

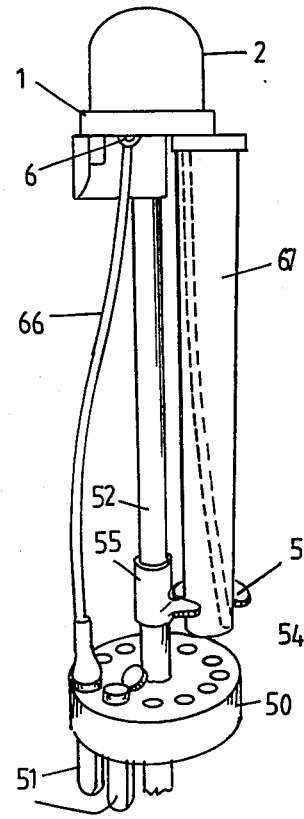
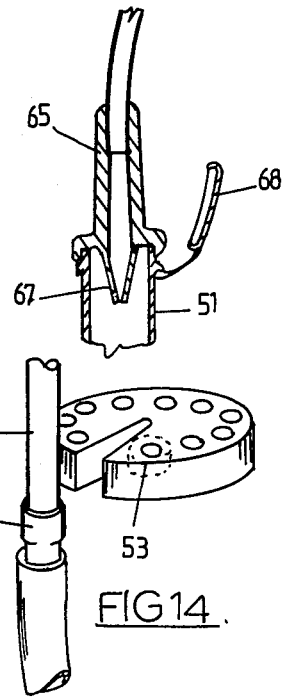
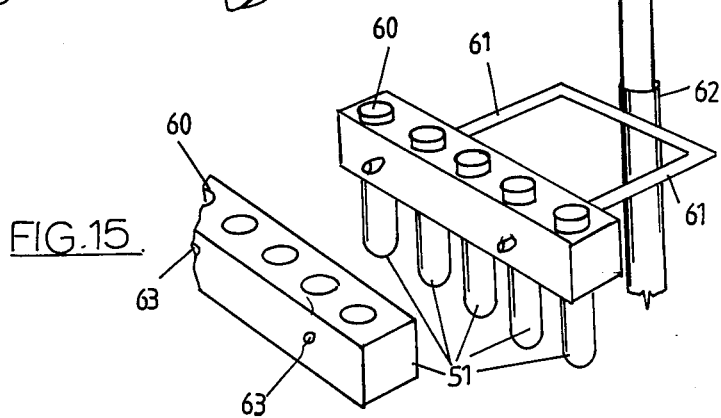

4,213,341

APPARATUS FOR SAMPLING A FLOW OF LIQUID FROM A FLUID AT LEAST SOME OF WHICH IS A LIQUID

This invention relates to apparatus for sampling a flow of liquid from a fluid at least some of which is a liquid and has been devised particularly though not solely for sampling milk from a cow.

It is an object of the present invention to provide apparatus for sampling a flow of liquid from a fluid at least some of which is a liquid which will at least provide the public with a useful choice.

Accordingly the invention consists in apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome, at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed flow and for each said flow dividing means an outlet port in said body arranged to collect from the area between two intermediate vanes in said flow dividing means, collecting means connected to said outlet port and further delivery means in said body arranged to collect and deliver from said body and dome the remainder of the fluid passing through said apparatus.

To those skilled in the art to which this invention relates, many changes in construction and widely differing embodiments and applications of the invention will suggest themselves without departing from the scope of the invention as defined in the appended claims. The disclosures and the description herein are purely illustrative and are not intended to be in any sense limiting.

Figure 2:
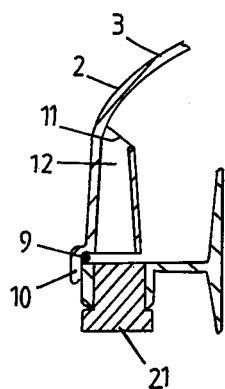
Figure 3:
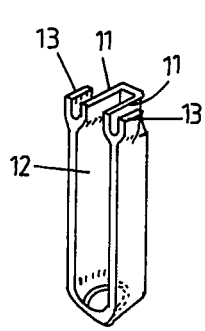
Figure 4:
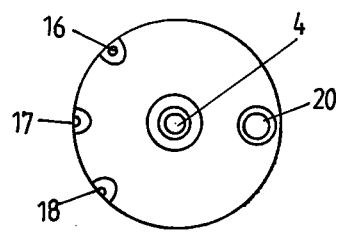
Figure 8:
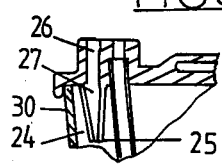
Figure 5:
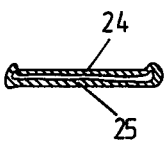

One preferred form of the invention will now be described with reference to the accompanying drawings in wich, FIG. 1 is a cross sectional view of one form of apparatus according to the invention;

FIG. 2 is a cross sectional view of a flow dividing means shown in FIG. 1 and with an outlet port closed off, FIG. 3 is a perspective view of a hollow member forming said flow divider, FIG. 4 is a plan view of the apparatus shown in FIG. 1, showing location of inlet and first and second conduit ports, FIG. 5 is a cross sectional view of a collapsible orifice leading to a sampling flask, FIG. 6 is a cross sectional view of one form of a connector and collecting vessel for use in the device shown in FIGS. 1 to 5, FIG. 7 is an alternative construction to that shown in FIG. 5, FIG. 8 is a scrap view of an alternative in the upper part of the construction shown in FIG. 6, FIG. 9 is a scrap view showing one form of air admitting means for the collecting vessel shown in FIG. 5 or FIG. 6, FIG. 10 is a cross sectional view of the construction shown in FIG. 9, FIG. 11 is an alternative construction to that shown in FIG. 9, FIG. 12 is a part view of the construction shown in FIG. 11, with a key thereof in the open disposition, FIG. 13 is a diagrammatic perspective view of a device according to FIGS. 1 to 4 with a fixed calibrated flask and sample collecting device associated therewith according to the invention, FIG. 14 is a perspective view showing a method of engagement between a circular magazine and a suitable support post therefor, FIG. 15 is a cross sectional view of a connector and flask for use in the magazine of FIG. 14 for use in the invention and, FIG. 16 is a perspective sketch of an alternative magazine arrangement.

Referring to the drawings apparatus for sampling a flow of liquid from a fluid at least some of which is a liquid will be described in connection with a milk meter in which the fluid comprises a pulsating mixture of milk and air from teat cups applied to a cow and connected to the meter through the usual cluster and milk pipe. Thus a body 1 has mounted on it a dome 2 having an inner flow distributing surface 3. An inlet conduit 4 has a delivery orifice 5 disposed above the conduit 4 and arranged symmetrically in relation to the dome 2 to deliver fluid into the space 6 and so that milk flows over the surface 3. Vanes 7 are provided to give a twisting or swirling movement to milk entering through conduit 4 so as to assist the formation of an even flow of milk over the inside surface 3 of the dome 2. In use the apparatus is arranged with the upper part of the dome 2 above the orifice 5 which in turn is above the conduit 4. The arrangement shown in FIG. 1 is such that there is a substantially even distribution of liquid from the fluid i.e. mixture of milk and air over the inner surface 3 of the dome 2. Thus the dome 2 preferably includes a planar section 8 and the orifice 5 is disposed close to the planar section 8. To seal the dome 2 to the body 1 a gasket 9 engages on surfaces of the body 1 and a flange 10 surrounds part of the body 1. Any suitable clamping means (not shown) is provided to clamp the dome 2 onto the body 1.

In order to collect a sample which is proportional to the volume of milk passing through the device it is necessary to insert a measuring orifice adjacent to part of the surface 3 of the dome 2 to collect a proportionate sample from the milk flow.

It is obvious that when a fluid flow is interrupted by obstructions whether they be the supporting piers of a bridge over a river or the lips 11 of a measuring orifice 12, a pressure wave will build up against the edge or surface of the obstruction i.e. over the surface of the lip 11 shown in FIG. 1. This pressure wave has an appreciable effect on flow distribution particularly with regard to flow in or through the collecting orifice 12 and this distribution tends to change with changes in the thickness or velocity of the film of milk. However if a uniformly flowing body of liquid is interrupted by a row of obstructions which give uniform obstruction to the flow of milk the flow between any two of the obstructions will be the same as that between any other two obstructions substantially irrespective of flow velocity, depth of film or any pressure waves which may form. Accordingly if the flow of milk on the surface 3 of the dome 2 is uniformly interrupted by vanes or pillars any intermediate pair of which may be the lips of a measuring orifice the milk flow between those lips will always or within very close limits be a consistent proportion of the total flow over the surface of the dome 2 and this proportion will be largely independent of flow velocity or volume variation.

In practice it has been found to be unnecessary to divide the dome all the way round its inner surface 3. It is usually adequate to provide a single additional vane 13 FIG. 3 or lip at each side of the collecting orifice 12 so that the vanes or lips 11 are intermediate vanes in a set comprising at least four vanes or lips, the spaces between adjacent vanes or lips being substantially equal.

It is preferable that part of the wall 14 of the dome 2 also acts as a part of the wall of the orifice 12 since this positions the orifice 12 against the inside surface of the dome 2 in which position it may be reliably moulded or affixed, is adequately protected against mechanical damage, is readily and easily cleaned and gives more accurate division of flow with the collecting orifice 12 situated in the substantially continuous flowing film. Furthermore as the result of mechanical protection afforded by this construction the thickness of the vanes 11 and 13 is not unduly restricted. The construction above described provides a flow divider which has been shown to offer excellent collection accuracy over a wide range of milk flows as would be encountered in a diverse dairy industry and over a range of air admissions at the milking cluster from zero to four times that passed through a standard air admission hole of 0.8 mm diameter. Furthermore because of the simplicity of the construction it is simple and practicable to provide two or more flow dividers within a single dome 2. Each of these flow dividers may collect a separate and if desired different sized sample without one flow divider having any effect on the other. Thus referring to FIG. 4 a plurality of outlet ports 16, 17 and 18 is provided, each leading to a sample container such as the container 19 FIG. 1 and in addition in FIGS. 1 and 4 is shown an outlet 20 through which milk and air remaining after the samples have been taken through outlets 16, 17 and 18 is passed from within the dome 2. If it is desired to use less than all of the outlets 16 to 18 one or more may be plugged with a rubber or elastomer plug 21 (FIG. 2). A space 22 is provided above the plug 21 when the latter is installed to assist in cleaning the passageway 12 by cleaning in place solutions.

Only a simple a collecting container or flask 19 is shown in FIG. 1 but other types of collecting flasks may be provided according to requirements which will vary from country to country or industry sector to industry sector. Some requirements are for a calibrated flask for easy reading and it is normal for this flask to collect 2 to 2½% of the milk throughput. Other requirements are for a smaller sample normally 0.5% to 0.75% to be collected in a readily removable flask which is then sealed and transported to a laboratory for analysis. Accordingly further constructions will shortly be described.

It is also desirable that, should a flask such as the flask 19 be removed, no closing of taps or other manually operable device be necessary to avoid a large in rush of air spoiling vacuum within the milking machine apparatus to which present apparatus is connected. Accordingly an outlet 22 is provided with resilient thin tapering walls and is formed in an elliptical manner at its end 23 so that if the container 19 is removed the inward rushing air flow caused by the difference in pressure between atmosphere and the milking line vacuum level inside the dome 2 will cause the thinned end to collapse or flatten with the faces 24 and 25 FIG. 5 partially sealing against each other to reduce the inflow of air. When a containuous is replaced and the differential pressure is removed by means of a slight leakage through the partial closure, the walls 24 and 25 will relax to an open position and allow milk to flow from the passageway 12 into the flask 19. This also permits atmospheric pressure outside the flask 19 to hold that flask onto the connector 26. The collecting flask 19 may be formed of a permanent re useable material such as polysulfone or poly carbonate or may be of low cost disposable material such as polystyrene or poly propylene.

Where the apparatus is to be operated with a large (2.0% to 2.5% of throughput) flask, for example, the flask 30 shown in FIG. 6 the milk is led to the bottom of the flask 30 by means of a small bore tube 31 to avoid air entrapment and agitation or frothing of the milk in the flask 30. The froth will float on the milk as is shown at 32 and be retained in the tube 31 as is shown at 32, while the milk flows through and reaches a level 33 according to the volume admitted. Tube 31 is retained in a moulded aperture 33 in the connecting member 34 and a groove 35 allows air flow between the interior of the flask 30 and the dome 2.

Alternatively as shown in FIG. 8 a separate air passageway 26 has an outlet 27 constructed in the same way as outlet 22.

In FIG. 7 a different flask 36 is shown having a tube 37 external of the flask and connected to the connecting head 38. Again an air tube 39 is provided and the tube 37 leads to a passageway 40 blocked with a plug 41 removable for cleaning purposes.

The flask 30 or 36 may be easily emptied by admitting air into the flask. In one construction a flap 40 is made of resilient material and may be turned to the position 41 (FIG. 10) and permits air to enter through the opening 42.

In an alternative construction a connector 43 (FIG. 11) has a slot 44 in it and a key 45. There is a resilient part 46 of the connector 43 the arrangement being such that on turning the key to the position shown in FIG. 12 the edge 47 of the part 46 is distorted to admit air into the container or flask 30 or 36. This enables admission of air with low risk of hygiene problems.

When the device is to be used to collect milk samples for analysis at some other place a smaller sample (typically 0.5% or 0.75%) of the throughput is required and a separate flask is used for each animal. Since it is sometimes considered that agitation of a milk sample during transport may have an affect on test results turbulence or agitation during transport would normally be at a lower level in a flask of narrow cross section. In these circumstances the flask may simply be a tube similar to a test tube.

The flasks may be conveniently arranged in rectangular or circular magazines and in FIG. 13 there is shown a circular magazine 50 containing flasks 51. The magazine 50 may be quickly mounted by placing such a magazine around a suitable member, for example, the central inlet tube 52 leading to the body 1 of the device and if desired a moulded recess 53 (FIG. 14) engages around a collar 54 on the pipe 52 or alternatively around the clip boss 55.

In an alternative construction shown in FIG. 15 a series of rectangular magazines 60 are mounted on tines 61 mounted on a column 62, the tines of course fitting in holes 63 in the magazines 60. Connection to each flask through which milk is supplied is through a connection 65 (FIG. 16) which is simply mounted on top of each flask 51 in turn, the magazine being rotated as desired and the connection 65 being connected through a tube 66 to the flange 26 (FIGS. 1 and 13). The connection 65 is simply held onto the flask 51 by atmospheric air pressure. When the animal has milked out the cover 65 is deflected or rotated sideways to break the seal between it and the flask 51 and crimped into the next flask which is moved into position by rotating the magazine or moving it along the line of flasks in the magazine as desired. A flexible orifice 67 is provided which collapses as above described to prevent undue entry of air during flask changes.

It will be apparent that a large flask such as flasks 30 and 36 may be mounted on the body 1 and have milk collecting in it at the same time as a small flask 51 is receiving milk and under these conditions an operator may read the quantity of milk in the large flask 15 and then rotate the key 45 while he is recording the quantity of milk and other data on top of the small flask 51 so that all the information is recorded and after changing the connector 65 to a new flask, the key 45 is returned so that the large flask 67 having been emptied can now be refilled from the next animal.

The filled flask 67 is closed off with cap 68 and the marking to identify the sample and quantity are made on the cap or otherwise as desired. Alternatively, the flask may be mounted directly by a connector to the device as is shown in FIG. 1, the flask being referenced 19 in that figure. Closures 68 may be captive or separate and if separate sample identification is simplified since there is no likelihood of an old identification not being changed for a new sample.

The operation of the construction is as follows:

The conduit 4 is connected to the milk tube 52 of a milking machine and the outlet 20 connected back to the milking machine, and fluid in the form of a mixture of milk and air then flows through the conduit 4 and proceeds from the orifice 5 and the milk is passed to the inner surface 3 of the dome 2 as a substantially even film. The measuring orifice or passageway 12 collects a sample of the milk, the vanes 13 assisting in the evenness of flow distribution and feeds it into a sampling flask, for example, the flask 19 in FIG. 1 or the other flasks shown and as stated a number of flasks may be provided in a single dome 2 if desired. Unsampled milk and air are led away through orifice 20. When an animal has been milked out the sampling flask is emptied by any of the methods above described and either the tube such as the tube 66 changed over to a new flask or the old flask renewed or re used after emptying by admitting air is above described.

The construction at least in the preferred form has many features and advantages.

1. Because the collector orifices have lips 11 intermediate of additional vanes, substantial accuracy is achieved by the invention, 2. A plurality of collector orifices may be mounted and such orifices are arranged upstream from the lower or trailing edge of the dome and not below or after that lower edge of the dome or any break in the flow of milk film across the internal surface of the dome as with present constructions resulting in increased accuracy.

3. A plurality of flasks may be quickly and easily connected to the sampling device so that these may be sampled one at a time or a plurality operated at the same time without interference of one with the other.

4. The flask connecting units may be installed under selected collecting orifices and/or replaced by blanking plugs.

5. Changes of flasks and emptying of the flasks is quickly achieved without the operation of taps and by minor changes in mode of operation of the apparatus.

6. For larger measuring flasks the collecting flasks are filled to and from the bottom by small bore tubes to give substantially foam free filling.

7. Larger measuring flasks are quickly emptied by admitting air to the flasks' upper ends.

8. Smaller flasks used for later analysis may be supported in a magazine and filled by means of a flexible tube and the magazines may be replaced quickly and easily.

I claim:

1. Apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed flow and for each said flow dividing means an outlet port in said body arranged to collect liquid from the area between two intermediate vanes in said flow dividing means, collecting means connected to said outlet port and further delivery means in said body arranged to collect and deliver from said body and dome the remainder of the fluid passing through said apparatus.

2. Apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed flow and for each said flow dividing means an outlet port in said body arranged to collect liquid from the area between two intermediate vanes in said flow dividing means, collecting means connected to said outlet port and further delivery means in said body arranged to collect and deliver from said body and dome the remainder of the fluid passing through said apparatus wherein a plurality of flow dividing means including an outlet port for each is provided and plug means are provided whereby one or more of said plurality of outlet means may be plugged if not in use and a cleaning space is provided between said outlet port and a plug when inserted.

3. Apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed flow and for each said flow dividing means an outlet port in said body arranged to collect liquid from the area between two intermediate vanes in said flow dividing means, collecting means connected to said outlet port and further delivery means in said body arranged to collect and deliver from said body and dome the remainder of the fluid passing through said apparatus wherein for each outlet port a resilient elliptical orifice leads to said collecting means and is arranged so that when the collecting means is removed the difference in air pressure between ambient air pressure and the interior of said dome causes the walls of said orifice to collapse preventing rapid ingress of air to said dome.

4. Apparatus as claimed in claim 1 wherein said collecting means comprises a flask having a liquid delivery tube passing from a connecting means on said flask to close to the bottom of the collecting flask, said connecting means including gas entry means to an upper part of said flask.

5. Apparatus as claimed in claim 1 wherein a magazine is detachably mounted on said apparatus, said magazine containing a plurality of flasks and a tube is connected between one of said outlet ports and the mouth of a selected sampling tube, the connecting tube being transferred from one sampling tube to a next sampling tube for successive tests or samples taken.

6. Apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed flow and for each said flow dividing means an outlet port in said body arranged to collect liquid from the area between two intermediate vanes in said flow dividing means, collecting means connected to said outlet port and further delivery means in said body arranged to collect and deliver from said body and dome the remainder of the fluid passing through said apparatus, the apparatus further including a magazine detachably mounted thereon, said magazine containing a plurality of flasks and a tube connected between one of said outlet ports and the mouth of a selected sampling tube, the connecting tube being transferred from one sampling tube to a next sampling tube for successive tests or samples taken wherein said magazine comprises a substantially circular magazine having a slot arranged to engage over a collar on mounting means associated with said apparatus.

7. Apparatus for sampling a flow of liquid from a fluid at least some of which is a liquid, said apparatus comprising a body, an inlet conduit in said body terminating in an inlet orifice, said conduit being arranged in use so that said conduit is substantially vertical and said orifice is above said conduit, a curved dome mounted in use above said orifice and arranged relative thereto so that liquid in fluid passed up said conduit and through said orifice is substantially evenly distributed over the inner surface of said dome at least one set of flow dividing means arranged relative to said flow distributing surface, each said flow dividing means comprising at least four vanes on said distributing surface arranged so that the rate of flow of liquid in the space between a pair of intermediate vanes of said at least four vanes is not substantially different from the rate of flow over an equivalent space elsewhere in said substantially evenly distributed to flow and for each said flow dividing means an outlet port in said body arranged to collect liquid from the area between two intermediate vanes in said flow dividing means, collecting means connected to said outlet port and further delivery means in said body arranged to collect and deliver from said body and dome the remainder of the fluid passing through said apparatus, the apparatus further including a magazine detachably mounted thereon, said magazine containing a plurality of flasks and a tube connected between one of said outlet ports and the mouth of a selected sampling tube, the connecting tube being transferred from one sampling tube to a next sampling tube for successive tests or samples taken wherein said magazine comprises a rectangular member having holes therein to receive sampling tubes and the apparatus including magazine mounting means comprising a forked member the tines of which are engaged in holes in said rectangular member.

* * * * *